United States Patent [19]

Chiodoni

[11] 4,455,432

[45] Jun. 19, 1984

[54] PROCESS FOR THE PREPARATION OF 1-(4-CHLORO-BENZOYL)-5-METHOXY-2-METHYL-3-INDOLYL-ACETOHYDROX-AMIC ACID

[75] Inventor: Ugo Chiodoni, Milan, Italy

[73] Assignee: Unibios S.p.A., Trecate, Italy

[21] Appl. No.: 360,819

[22] Filed: Mar. 22, 1982

[30] Foreign Application Priority Data

Apr. 3, 1981 [IT] Italy .............................. 20918 A/81

[51] Int. Cl.$^3$ ............................................ C07D 209/28
[52] U.S. Cl. .................................. 548/501; 548/494; 548/502; 564/133; 260/500.5 H
[58] Field of Search .................... 548/501, 502, 494; 564/133; 260/500.5 H

[56] References Cited

U.S. PATENT DOCUMENTS

| | | | |
|---|---|---|---|
| 2,397,508 | 4/1946 | Rouault et al. | 260/500.5 H |
| 2,785,191 | 3/1957 | Schwyzer | 260/500.5 H |
| 3,624,103 | 11/1971 | De Martiis | 548/494 |
| 3,962,471 | 6/1976 | Biere et al. | 548/501 |
| 4,186,133 | 1/1980 | Tamietto | 548/501 |

*Primary Examiner*—Paul M. Coughlan, Jr.
*Assistant Examiner*—D. B. Springer
*Attorney, Agent, or Firm*—Walter H. Schneider

[57] ABSTRACT

A new process for the preparation of the 1-(4-chloro-benzoyl)-5-methoxy-2-methyl-3-indolyl-acetohydrox-amic acid, which comprises reacting the reaction product of 1-(4-chloro-benzoyl)-5-methoxy-2-methyl-3-indolyl-acetic acid and an alkyl-halocarbonate, with hydroxylamine.

3 Claims, No Drawings

PROCESS FOR THE PREPARATION OF 1-(4-CHLORO-BENZOYL)-5-METHOXY-2-METHYL-3-INDOLYL-ACETOHYDROXAMIC ACID

DESCRIPTION OF THE INVENTION

The present invention refers to a new and improved process for the preparation of the 1-(4-chloro-benzoyl)-5-methoxy-2-methyl-3-indolyl-acetohydroxamic acid of formula (I)

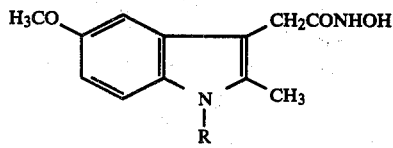

wherein R is the 4-chlorobenzoyl group.

This substance is also known as oxamethacin (INN-=International Non-proprietary Name) and is a drug possessing acknowledged antinflammatory properties.

A process for the preparation of the compound of formula (I) has already been described in U.S. Pat. No. 3,624,103. This process is essentially based on the reaction between the chloride of the 1-(4-chloro-benzoyl)-5-methoxy-2-methyl-3-indolyl-acetic acid and hydroxylamine, according to the following reaction scheme 1

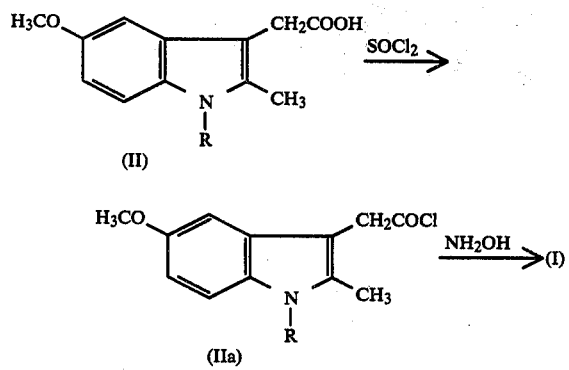

wherein R is the 4-chlorobenzoyl group.

The improved process according to the present invention for preparing the compound of the above formula (I) is characterized in that a compound of the formula (IV) obtained by reacting 1-(4-chlorobenzoyl)-5-methoxy-2-methyl-3-indolyl-acetic acid and an alkyl halocarbonate is reacted with hydroxylamine, as it is illustrated in the following scheme 2

SCHEME 2

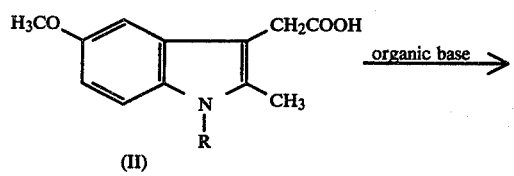

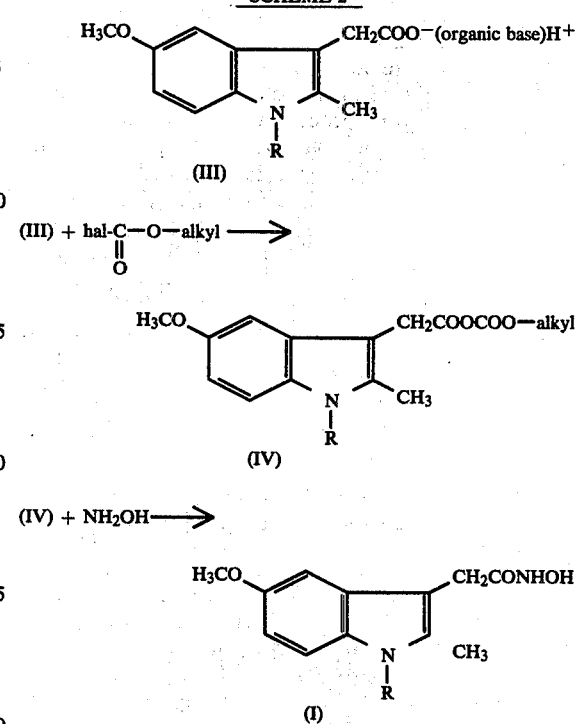

wherein R is the 4-chlorobenzoyl group.

In the above scheme 2, "hal" represents a halogen atom, preferably chlorine or bromine and "alkyl" stands for methyl, ethyl, propyl, isopropyl, butyl, isobutyl or sec.-butyl and, preferably, ethyl. The organic base is essentially a tertiary nitrogen containing base commonly employed in such types of reactions, as an example trimethylamine, triethylamine, pyridine, the picolines, preferably, triethylamine.

According to the above scheme 2, a molar proportion of the 1-(4-chloro-benzoyl)-5-methoxy-2-methyl-3-indolyl-acetic acid of formula (II) is contacted with a substantially equimolecular amount of a predetermined alkyl halocarbonate in the presence of a tertiary organic nitrogen containing base which is added to the reaction mixture in substantially equimolecular ratios as well. The organic base has the purpose of first salifying the starting indolyl-acetic acid of formula (II) and, subsequently, blocking the acidity which develops during the reaction course by formation of the corresponding hydrohalide, which may or not be eliminated from the reaction mixture without affecting the yields of the entire process.

Also the so obtained compound of formula (IV) needs not to be isolated for the subsequent condensation step. As a matter of fact, a molar quantity, or a slight molar excess of hydroxylamine calculated over the starting indolyl-acetic acid of formula (II), is added to the reaction mixture, which is subsequently stirred vigorously for some hours until the reaction is completed.

The reactions are carried out in inert organic solvents, as an example lower halogenated hydrocarbons, benzene, toluene, xylene and mixtures thereof, preferably, chloroform. The temperature interval is advantageously selected between about −10° and 50° C.

Compared with the method as described in U.S. Pat. No. 3,624,103, the process of the present invention possesses remarkable advantages. As an example, the yields by weight of the final product are never lower than 90%, calculated over the starting indolyl-acetic acid of formula (II), whereas the corresponding yields obtained with the art process barely reach 70%. Moreover, the amounts of reactants i.e., the alkyl halocarbonate and hydroxylamine, are considerably lower than the corresponding amounts of thionyl chloride and hydroxylamine used in the known process. Incidentally, it must also be pointed out that thionyl chloride is a poisonous and irritating agent which has to be handled with the utmost care. Finally, the compound of formula (IV), contrary to the acyl chloride of formula (IIa), needs not to be isolated and can be used as such for the subsequent condensation step with hydroxylamine, so that the total reaction times are considerably shortened.

The following examples are given with the purpose of better illustrating the invention but in no way they must be construed as a limitation of the scopes of the invention itself.

EXAMPLE 1

In a four-necked flask equipped with a mechanical stirrer, a dropping funnel, a cooler with $CaCl_2$ tube and thermometer, there was poured a solution of 230 g (0.637 mole) of 1-(4-chloro-benzoyl)-5-methoxy-2-methyl-3-indolyl-acetic acid and 88.2 ml (0.637 mole) of triethylamine in 400 ml of chloroform. This solution was added dropwise with stirring to a solution of 60.7 ml (0.637 mole) of ethyl chlorocarbonate, keeping the temperature low by an external cooling of ice and water. The formed triethylamine hydrochloride was removed by filtration, then the chloroform solution was added at room temperature to 21.12 g (0.64 mole) of hydroxylamine. After stirring for some hours, the formed precipitate was recovered by filtration, washed with chloroform, dried and subsequently washed several times with water in order to remove the inorganic residues. After drying in oven, 210 g (yield 91% by weight) of pure oxamethacin were obtained. M.p. 181°–83° C.

EXAMPLE 2

By operating substantially as described in the foregoing example, but using toluene instead of chloroform as the reaction solvent, the desired product (oxamethacin) was obtained with a 88% yield.

EXAMPLE 3

The same procedure as in Example 1 was repeated, but the triethylamine hydrochloride was not isolated. The final yield was 89.2%.

I claim:

1. A process for the preparation of 1-(4-chlorobenzoyl)-5-methoxy-2-methyl-3-indolyl-acetohydroxamic acid which comprises the steps of: bringing together 1-(4-chlorobenzoyl)-5-methoxy-2-methyl-3-indolyl-acetic acid and a lower alkylhalocarbonate in the presence of a tertiary organic nitrogen base and an inert organic solvent with agitation and for a period of time sufficient to form a reaction mixture comprising an anhydride reaction product; without isolating said anhydride reaction product, adding hydroxylamine thereto with agitation for a period of time sufficient to form 1-(4-chlorobenzoyl)-5-methoxy-2-methyl-3-indolyl-acetohydroxamic acid; and recovering said acetohydroxamic acid, the several reactants being employed in substantially equimolecular amounts and the reaction steps being conducted in a temperature range of −10° to 50° C.

2. A process according to claim 1 in which the anhydride reaction product is isolated before the addition of hydroxylamine thereto.

3. A process according to claim 1 or 2 in which the lower alkylhalocarbonate is ethylchlorocarbonate, the tertiary organic nitrogen base is triethylamine, and the organic solvent is chloroform.

* * * * *